(12) United States Patent
Oguma

(10) Patent No.: US 8,866,095 B2
(45) Date of Patent: Oct. 21, 2014

(54) RADIOGRAPHIC IMAGING APPARATUS

(75) Inventor: Kumiko Oguma, Kunitachi (JP)

(73) Assignee: Konica Minolta Medical & Graphic, Inc. (JP)

( * ) Notice: Subject to any disclaimer, the term of this patent is extended or adjusted under 35 U.S.C. 154(b) by 471 days.

(21) Appl. No.: 13/380,310

(22) PCT Filed: Feb. 24, 2010

(86) PCT No.: PCT/JP2010/052840
§ 371 (c)(1),
(2), (4) Date: Dec. 22, 2011

(87) PCT Pub. No.: WO2011/001705
PCT Pub. Date: Jun. 1, 2011

(65) Prior Publication Data
US 2012/0097860 A1   Apr. 26, 2012

Related U.S. Application Data

(66) Substitute for application No. PCT/JP2010/052840, filed on Feb. 24, 2010.

(30) Foreign Application Priority Data

Jul. 1, 2009   (JP) ................................. 2009-156664

(51) Int. Cl.
*G01T 1/16* (2006.01)
*H04N 5/357* (2011.01)
*A61B 6/00* (2006.01)
*H04N 5/32* (2006.01)
*H04N 5/374* (2011.01)

(52) U.S. Cl.
CPC *H04N 5/357* (2013.01); *G01T 1/16* (2013.01); *A61B 6/4233* (2013.01); *A61B 6/4283* (2013.01); *H04N 5/32* (2013.01); *H04N 5/374* (2013.01)
USPC ............ 250/370.09; 250/370.11; 250/370.14

(58) Field of Classification Search
CPC ......... H04N 5/32; H04N 5/357; H04N 5/374; G01T 1/16
USPC ............................ 250/370.09, 370.11, 370.14
See application file for complete search history.

(56) References Cited

U.S. PATENT DOCUMENTS

| 7,193,219 B2* | 3/2007 | Schick et al. ............ 250/370.11 |
| 7,211,803 B1 | 5/2007 | Dhurjaty et al. |
| 2003/0086523 A1 | 5/2003 | Tashiro et al. |
| 2004/0066898 A1 | 4/2004 | Schick et al. |
| 2011/0317809 A1* | 12/2011 | Eguchi ............................ 378/62 |

FOREIGN PATENT DOCUMENTS

| JP | 6-342099 A | 12/1994 |
| JP | 9073144 A | 3/1997 |

(Continued)

OTHER PUBLICATIONS

International Search Report for International Application No. PCT/JP2010/052840 mailed Mar. 30, 2010 with English translation.

*Primary Examiner* — Casey Bryant
(74) *Attorney, Agent, or Firm* — Cantor Colburn LLP

(57) ABSTRACT

Provided is a radiographic imaging apparatus capable of obtaining more suitable radiological images by reducing the influence of noise generated at a current detecting section which detects current carried by applying radiation. The radiographic imaging apparatus includes a plurality of radiation detection elements two-dimensionally arranged in each region defined by a scanning line and a signal line, a switch section the state of which is switched between on and off states depending on voltage applied to the connected scanning line, a scan drive means having a gate driver that applies on voltage and off voltage to the switch section through the scanning line and a power supply circuit that supplies on voltage and off voltage to the gate driver, a current detecting section for detecting current flowing between the power supply circuit and the gate driver or current flowing through the scanning line, and a control section for detecting at least the start of applying radiation on the basis of the value of the current detected by the current detecting section.

10 Claims, 7 Drawing Sheets

(56) References Cited

FOREIGN PATENT DOCUMENTS

| | | |
|---|---|---|
| JP | 11-155847 A | 6/1999 |
| JP | 2003-126072 A | 5/2003 |
| JP | 2006-505308 A | 2/2006 |
| JP | 2006-58124 A | 3/2006 |
| WO | WO 2011086826 A1 * | 7/2011 |
| WO | WO 2011104991 A1 * | 9/2011 |

* cited by examiner

RADIOGRAPHIC IMAGING APPARATUS

CROSS REFERENCE TO RELATED APPLICATIONS

This is a U.S. National Phase Application under 35 U.S.C. 371 of International Application PCT/JP 2010/052840, filed on Feb. 24, 2010. This application claims the priority of Japanese Application No. 2009-156664 filed on Jul. 1, 2009, the entire content of which is hereby incorporated by reference.

TECHNICAL FIELD

The present invention relates to a radiographic imaging apparatus, particularly to a radiographic imaging apparatus capable of detecting the start of irradiation.

BACKGROUND TECHNOLOGY

Various developments having been disclosed so far include, for example, a so-called direct type radiation imaging apparatus wherein an electric charge is generated by a detection element in response to the dosage of the radiation such as X-ray having been applied, and is converted into an electric signal, or a so called indirect type radiation imaging apparatus wherein, after the applied radiation has been converted into the electromagnetic wave of another wavelength such as visible light by a scintillator and others, an electric charge is generated by a photoelectric conversion element such as a photodiode in response to the energy of the electromagnetic wave having been converted and applied, and is converted into electric signals. In the present invention, both the detection element in the direct type radiation detection element and the detection element in the indirect type radiation detection element are collectively called a radiation detection element.

The radiographic imaging apparatus of this type has been known under the name of FPD (Flat Panel Detector). This apparatus has been formed integral with a support base (or Bucky's radiological device) (Patent Literature 1). The development in recent years includes a portable radiographic imaging apparatus wherein the radiation detection element and others are accommodated in a housing. This has been put into practical use (Patent Literatures 2 and 3).

Incidentally, in some of the aforementioned radiographic imaging apparatuses, particularly portable radiographic imaging apparatuses, information on the start and termination of irradiation is sent to the radiographic imaging apparatus from an irradiation apparatus or an external device such as a computer for managing the system. After application of radiation in the radiographic imaging apparatus in response thereto, the image data is read from each of the radiation detection elements.

However, the aforementioned structure requires an interface to be provided between the irradiation apparatus or computer and the radiographic imaging apparatus so that control is provided by the overall system including the irradiation apparatus and computer. This will result in a large and complicated structure wherein the radiographic imaging apparatus recognizes the start and termination of irradiation. Thus, it is desirable to work out a structure that permits the start and termination of irradiation to be identified by the radiographic imaging apparatus itself.

In this case, the radiographic imaging apparatus can be provided with a sensor or the like to identify the start and termination of the irradiation. However, this structure requires a space for installing a sensor inside the radiographic imaging apparatus, with the result that the apparatus is increased in size. Further, if a sensor is provided, the power for driving the sensor is required. Particularly, the portable radiographic imaging apparatus has a problem of the built-in battery being consumed.

A solution to this problem has been proposed (Patent Literature 4). To be more specific, means are provided to detect the current flowing through the bias line for applying a bias voltage to each of the radiation detection elements. There is an increase of current flowing through the bias line when an electric charge is generated inside the radiation detection elements by irradiation. Thus, the start and termination of the irradiation is identified by detecting this change in the current value. This structure ensures easy identification of the start and termination of irradiation and reduced power consumption by providing the existing wiring with a current detecting section.

PRIOR ARTS

Patent Document

Patent Literature 1: Japanese Unexamined Patent Application Publication No. Hei 9 (1997)-73144
Patent Literature 2: Japanese Unexamined Patent Application Publication No. 2006-58124
Patent Literature 3: Japanese Unexamined Patent Application Publication No. Hei 6 (1994)-342099
Patent Literature 4: Specification U.S. Pat. No. 7,211,803

SUMMARY OF THE INVENTION

Problems to be Solved by the Invention

However, if a bias line is provided with a current detecting section to detect the start and termination of irradiation by changes in current value, as described above, noise generated by the current detecting section will be superimposed on the bias current applied to the radiation detection element through the bias line, and this will be applied. Since the noise of voltage generated by the current detecting section is superimposed as a noise charge on the electric charge generated inside the radiation detection element, the impact of the noise charge may deteriorate the quality of the finally obtained radiological image, the granularity thereof in particular.

To increase the resolution of the radiological image, the aforementioned radiographic imaging apparatus is designed in such a way as to maximize the area of the light converging surface of a diode and others in a limited space, in order to maximize the light converging efficiency when considered from the viewpoint of each of the radiation detection elements, although each radiation detection element is formed in a smaller configuration. This results in a greater parasitic capacitance of the radiation detection element.

Thus, when the bias line is provided with a current detecting section, as described above, the voltage noise generated from the current detecting section, i.e., the noise with respect to the bias voltage is, so to speak, amplified at a greater parasitic capacitance C according to the relationship of $Q=CV$, and is turned into a greater electric charge of noise, which is superimposed on the electric charge generated inside the radiation detection element by irradiation. This may further encourage reduction in quality of the finally obtained radiological image.

If the quality of the radiological image is deteriorated and the granularity in particular is aggravated and diagnosis is performed using such a radiological image, a diagnostic error may occur; for example, a lesion may be overlooked or a normal site is mistaken for a lesion. To avoid such an error, the radiographic imaging apparatus is expected to produce a radiological image of appropriate quality wherein the impact of noise is minimized.

In view of the problems described above, it is an object of the present invention to provide a radiographic imaging apparatus capable of obtaining more suitable radiological images by reducing the influence of the noise generated at a current detecting section that detects the current for detecting the start and termination of irradiation.

Means for Solving the Problems

To solve the aforementioned problem, the radiographic imaging apparatus of the present invention includes: a plurality of scanning lines; a plurality of signal lines; arranged to cross each other; a plurality of radiation detection elements two-dimensionally arranged in each region defined by the plurality of scanning lines and the plurality of signal lines; a switch section which is arranged for each of the plurality of radiation detection elements and which is switched between on-state and off-state depending on a voltage applied to the connected scanning line, wherein an electric charge generated in the radiation detection element is maintained in the off-state and is released in the on-state; a scan drive section having a gate driver that applies an on-voltage and an off-voltage to the switch section through the scanning line, and a power supply circuit that supplies said on-voltage and said off-voltage to the gate driver; a current detecting section for detecting a current flowing between the power supply circuit and the gate driver or a current running through the scanning line; and a control section for detecting at least a start of irradiation on a basis of a value of the current detected by the current detecting section.

Advantages of the Invention

In the radiographic imaging apparatus of the present invention, a current detecting section for detecting the start of irradiation is provided between the power supply circuit of the scan drive section and gate driver or on each of the scanning lines so as to detect the current running through each of the scanning lines. This configuration drastically reduces the electric charge of noise generated on the switch section due to the voltage noise generated by the current detecting section, taking advantage of the fact that the parasitic capacitance formed on the switch section is much smaller than a greater parasitic capacitance on the portion of a photo diode.

Thus, even if a very small electric charge of noise generated at the switch section is transmitted to the radiation detection element and is superimposed on the electric charge generated at the photo diode of the radiation detection element, the impact is very small as compared with the case of the conventional art wherein the noise with respect to the bias voltage caused by the current detecting section produced on the bias line is amplified by the greater parasitic capacitance of the radiation detection element, and a greater noise is superimposed thereon.

As described above, the present invention provides a structure wherein only a very small amount of the voltage noise generated at the current detecting section is superimposed on the finally obtained image data read out from each of the radiation detection elements. This ensures a positive reduction in the impact of the electric charge of noise, and provides a surefire means for avoiding the problem of deteriorating the quality of the finally obtained radiological image, the granularity thereof in particular.

DETAILED DESCRIPTION OF THE PREFERRED EMBODIMENTS

The following describes the embodiments of the radiographic imaging apparatus of the present invention with reference to the drawings.

The following describes the so-called indirect type radiographic imaging apparatus wherein the radiographic imaging apparatus is provided with a scintillator, and the applied radiation is converted into the electromagnetic wave of another wavelength such as visible light, whereby an electric signal is obtained. It should be noted that the present invention also applies to the direct type radiographic imaging apparatus. Further, a portable type radiographic imaging apparatus will be described. The description applies to the radiographic imaging apparatus formed integrally with the support base.

Figure 1:
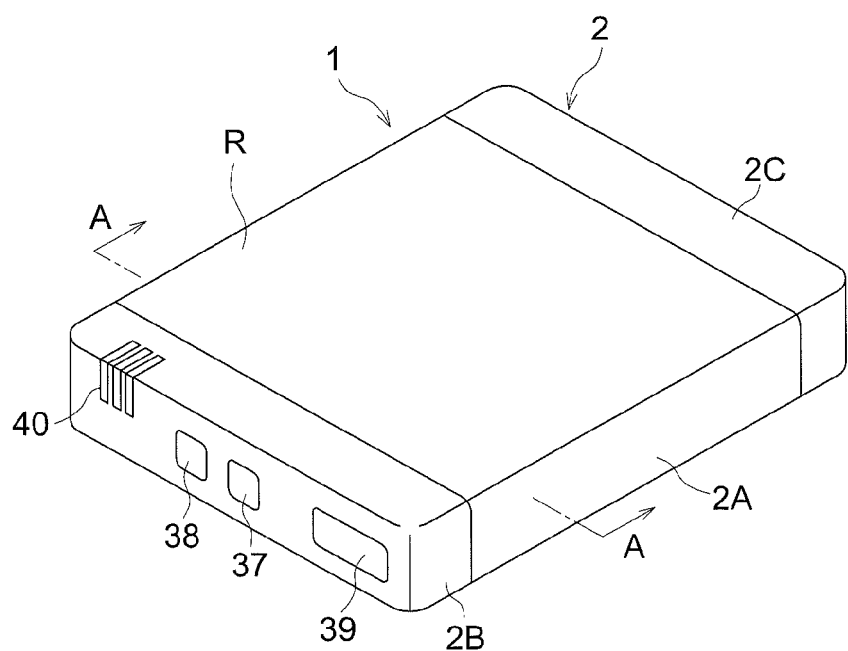
FIG. 1 is a perspective view representing a radiographic imaging apparatus of each of the embodiments.
Figure 2:
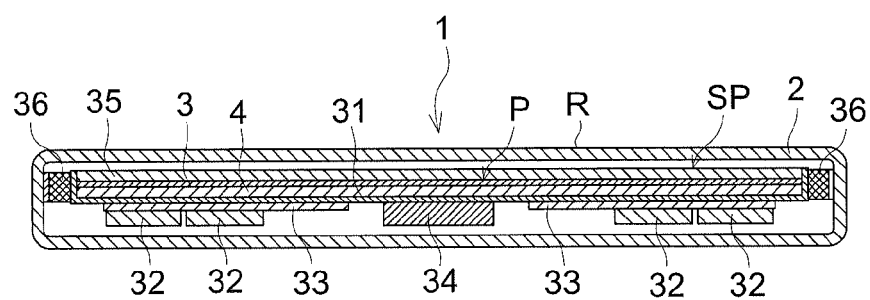
FIG. 2 is a cross section taken along arrow line A-A of FIG. 1.

FIG. 1 is a perspective view representing a radiographic imaging apparatus of the present embodiment. FIG. 2 is a cross section taken along arrow line A-A of FIG. 1. The radiographic imaging apparatus 1 of the present embodiment is designed as a portable (cassette) apparatus with a scintillator 3 and substrate 4 housed in the enclosure 2, as shown in FIG. 1 and FIG. 2.

At least the surface R of the enclosure 2 on the side exposed to radiation (hereinafter referred to as "radiation input surface R") is formed of a carbon board and plastic material capable of allowing passage of radiation. FIGS. 1 and 2 show a so-called "lunch box" type wherein the enclosure 2 is made of a frame plate 2A and back plate 2B. This can be replaced by a so-called monocock type wherein the enclosure 2 is formed integrally in the form of a rectangular sleeve.

Further, as shown in FIG. 1, the side of the enclosure 2 is provided with a power switch 36, an indicator 37 composed of a LED and others, and a cover member 38 which can be opened and closed for replacement of an unillustrated battery 40 (refer to FIG. 7 to be described later). In the present embodiment, an antenna device 39 as a means of communication with an external device is embedded in the side of the cover member 38.

As shown in FIG. 2, a base 31 is arranged inside the enclosure 2 through an unillustrated thin lead plate located below the substrate 4. The base 31 is provided with a PCB 33 (printed circuit board) equipped with electronic parts 32 and a buffer member 34. In the present embodiment, the radiation input surface R of the substrate 4 and scintillator 3 is provided with a glass substrate 35 for protection.

The scintillator 3 is bonded on the detection section (to be described later) of the substrate 4. The scintillator 3 used in the present embodiment is mainly composed of fluorophore. When the scintillator 3 is exposed to radiation, the radiation is converted into an electromagnetic wave having a wavelength of 300 through 800 nm, i.e., the electromagnetic wave mainly composed of visible light, and is outputted.

Figure 3:
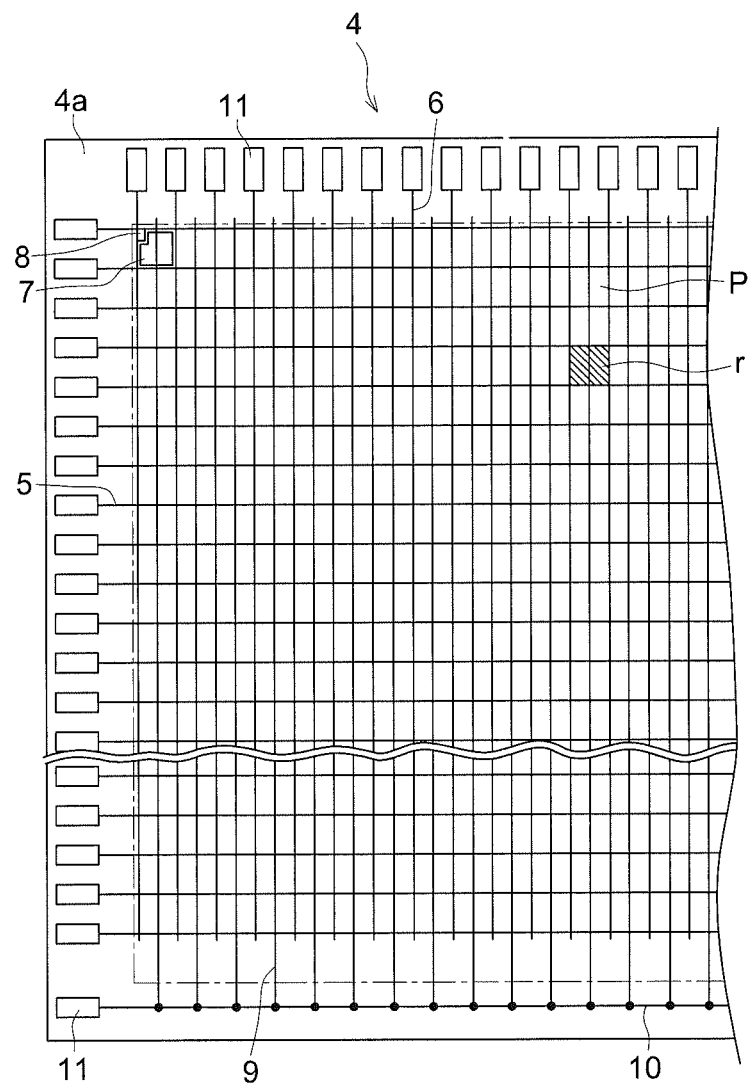
FIG. 3 is a plan view showing the structure of a substrate in the present embodiment.

In the present embodiment, the substrate 4 is made of a glass substrate, as shown in FIG. 3. A plurality of scanning lines 5 and signal lines 6 are arranged on the surface 4a opposed to the scintillator 3 of the substrate 4 so as to cross with each other alternately. A radiation detection element 7 is provided in each of small areas r defined by a plurality of scanning lines 5 and signal lines 6 of the substrate 4.

The overall region r provided with a plurality of radiation detection elements 7 arranged in a two-dimensional array in each of the small areas r defined by a plurality of scanning lines 5 and signal lines 6, i.e., the area indicated by a one-dot chain line in FIG. 3 is represented as a detection section P.

In the present embodiment, a photo diode is used as a radiation detection element 7. A phototransistor can also be used. As shown in the enlarged views of FIGS. 3 and 4, the radiation detection element 7 is connected with the source electrode 8s of a TFT 8 as a switch section. Further, the drain electrode 8d of a TFT 8 is connected with the signal line 6.

The TFT 8 is turned into the on-state when on-voltage is applied to the connected scanning line 5 by the scan drive section 15 (to be described later) and on-voltage is applied to the gate electrode 8g. The electric charge generated by the radiation detection element 7 and accumulated therein is discharged to the signal line 6. Further, the TFT 8 is turned into the off-state when off-voltage is applied to the connected scanning line 5 and off-voltage is applied to the gate voltage 8g. This suspends discharge of the electric charge from the radiation detection element 7 to the signal line 6, so that the electric charge generated in the radiation detection element 7 is maintained and is accumulated in the radiation detection element 7.

Figure 4:
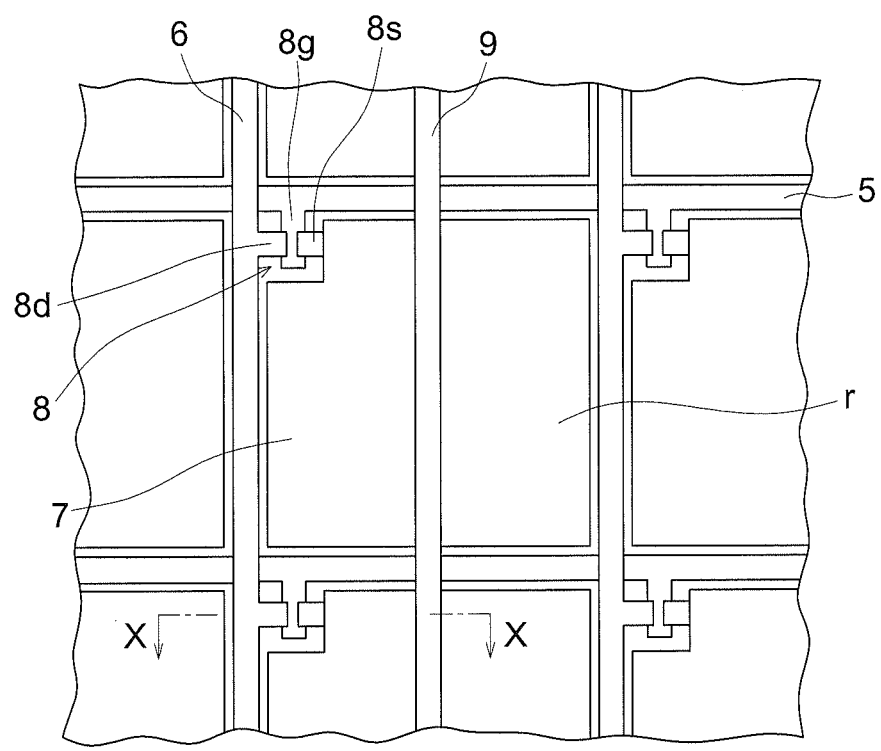
FIG. 4 is an enlarged view showing the structure of the radiation detection element and the TFT (thin film transistor) formed in a small region on the substrate of FIG. 3.
Figure 5:
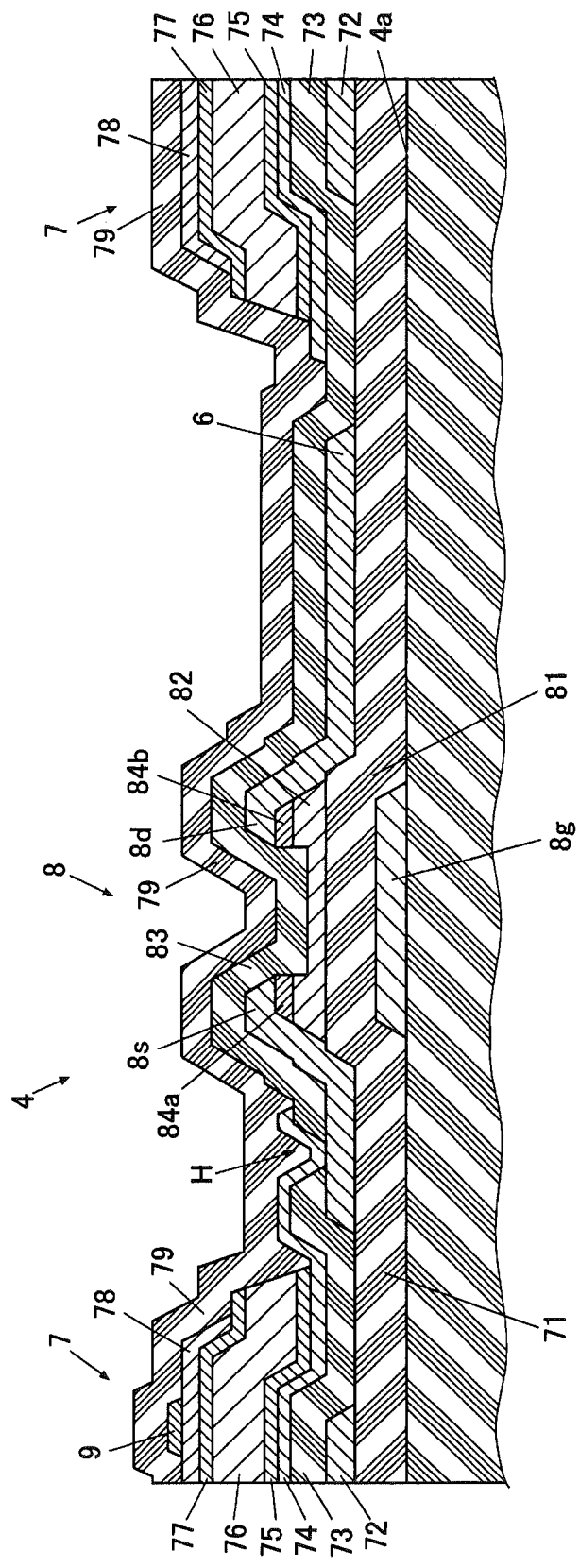
FIG. 5 is a cross section taken along arrow line X-X of FIG. 4.

Referring to the cross sectional view of FIG. 5, the following briefly describes the structure of the radiation detection element 7 and TFT 8. FIG. 5 is a cross section taken along arrow line X-X of FIG. 4.

The gate electrode 8g of the TFT 8 made of aluminum or chromium is laminated integrally with the scanning line 5 on the surface 4a of the substrate 4. The source electrode 8s connected with a first electrode 74 of the radiation detection element 7 and the drain electrode 8d formed integrally with the signal line 6 are laminated on the upper portion of the gate electrode 8g on the gate insulating layer 81 made of silicon nitride ($SiN_x$) laminated on the gate electrode 8g and surface 4a through the semiconductor 82 made of amorphous silicon hydride (a-Si).

The source electrode 8s and drain electrode 8d are divided by a first passivation layer 83 made of silicon nitride ($SiN_x$). The first passivation layer 83 covers both the electrodes 8s and 8d from the top. Further, ohmic contact layers 84a and 84b wherein an n-type material is formed by doping a Group VI element with the amorphous silicon hydride are laminated between the semiconductor 82 and source electrode 8s, and between the semiconductor 82 and drain electrode 8d, respectively. The TFT 8 is formed in the aforementioned manner.

In the radiation detection element 7, aluminum or chromium are laminated on the insulating layer 71 formed integrally with the gate insulating layer 81 on the surface 4a of the substrate 4 so that an auxiliary electrode 72 is formed. A first electrode 74 made of aluminum, chromium and molybdenum is laminated on the auxiliary electrode 72 wherein an insulating layer 73 formed integrally with the first passivation layer 83 is located in-between. The first electrode 74 is connected to the source electrode 8s of the TFT 8 through the hole H formed on the first passivation layer 83.

An n-layer 75 formed as an n-type by doping a Group VI element with the amorphous silicon hydride, an i-layer 76 as a converged layer formed of amorphous silicon hydride, and a p-layer 77 formed as a p-type by doping a Group III element with the amorphous silicon hydride are laminated on the first electrode 74 sequentially from the bottom.

Radiation is inputted from the radiation input surface R of the enclosure 2 of the radiographic imaging apparatus 1, and is converted into such an electromagnetic wave as visible light by the scintillator 3. When the converted electromagnetic wave is applied from above in the drawing, the electromagnetic wave reaches the i-layer 76 of the radiation detection element 7 and an electron-hole pair is generated inside the i-layer 76. In this manner, the radiation detection element 7 ensures that the electromagnetic wave applied from the scintillator 3 is converted into an electric charge.

The second electrode 78 as a transparent electrode such as an ITO is laminated on the p-layer 77 so that the applied electromagnetic wave reaches the i-layer 76. In the present embodiment, the radiation detection element 7 is formed in the manner described above. The order of the p-layer 77, i-layer 76 and n-layer 75 can be reversed. Further, in the above description, a so-called pin-type radiation detection element formed by lamination in the order of the p-layer 77, i-layer 76 and n-layer 75 described above is used as the radiation detection element 7 in the present embodiment. However, the present invention is not restricted to this description.

A bias line 9 for applying bias voltage to the radiation detection element 7 through the second electrode 78 is connected to the upper side of the second electrode 78 of the radiation detection element 7. The second electrode 78 of the radiation detection element 7, the bias line 9, the first electrode 74 extending toward the TFT 8 and the first passivation layer 83 of the TFT 8, i.e., the upper sides of the radiation detection element 7 and TFT 8 are covered with a second passivation layer 79 made of silicon nitride ($SiN_x$) from the upper side.

In the present embodiment, one bias line 9 is connected to a plurality of the radiation detection elements 7 arranged in a row, as shown in FIGS. 3 and 4. Each of the bias lines 9 is arranged in parallel with the signal line 6. Further, the bias lines 9 are bound by one connection line 10 outside the detecting section P of the substrate 4.

Figure 6:
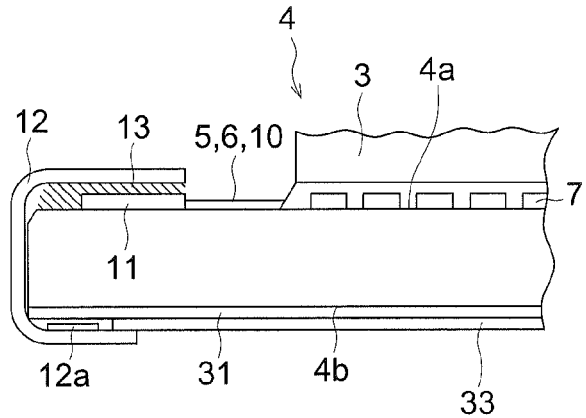
FIG. 6 is a side view showing the substrate with a COF and PCB mounted thereon.

In the present embodiment, the connection line 10 of the scanning line 5 and signal line 6 and bias line 9 are connected to the input/output terminal 11 (also referred to as a pad) arranged close to the edge of the substrate 4, as shown in FIG. 3. Each input/output terminal 11 is connected with the COF 12 (Chip On Film) having a built-in chip such as a gate IC 12a serving as a gate driver 15b of the scan drive section 15, through an anisotropic conductive adhesive material 13 such as an anisotropic conductive film or anisotropic conductive paste, as shown in FIG. 6.

The COF 12 is routed toward the rear surface 4b of the substrate 4 and is connected to the aforementioned PCB 33 on the rear surface 4b. In this manner, the substrate 4 of the radiographic imaging apparatus 1 is formed. It should be noted that electronic parts 32 are not illustrated in FIG. 6.

The following describes the circuit structure of the radiographic imaging apparatus 1. FIG. 7 is a block diagram showing the equivalent circuit of the radiographic imaging apparatus 1 in the present embodiment. FIG. 8 is a block diagram showing equivalent circuit for one pixel constituting the detecting section P.

As described above, the radiation detection elements 7 of the detecting section P of the substrate 4 have a second electrode 78 which are connected with the bias lines 9. Each bias line 9 is bound by the connection line 10 and is connected the bias power source 14. The bias power source 14 applies bias voltage to the second electrode 78 of each radiation detection element 7 through the connection line 10 and bias line 9.

In the present embodiment, the bias line 9 is connected to the side of the p-layer 77 (FIG. 7) of the radiation detection element 7 through the second electrode 78. This shows that a voltage (so-called reverse bias voltage) equal to or smaller than the voltage applied to the first electrode 74 side of the radiation detection element 7 is applied as the bias voltage to the second electrode 78 from the bias power source 14 through the bias line 9.

In the present embodiment, the bias power source 14 is connected to a main control section 22 and a sub-control section 23 (to be described later). The main control section 22 and sub-control section 23 are capable of changing the bias voltage applied to each radiation detection element 7 applied from the bias power source 14, wherever required.

The first electrode 74 of each radiation detection element 7 is connected to the source electrode 8s ("S" in FIGS. 7 and 8) of the TFT 8. The gate electrodes 8g ("G" in FIGS. 7 and 8) of TFT 8 are connected to the lines L1 through Lx of each scanning line 5 extending from the gate driver 15b of the scan drive section 15 (to be described later). The drain electrodes 8d ("D" in FIGS. 7 and 8) of each TFT 8 are connected to the signal lines 6.

In the present embodiment, the scan drive section 15 is provided with the power circuit 15a and gate driver 15b, and is designed to control the on- and off-voltages applied to the gate electrode 8g through the scanning line 5 connected to the gate driver 15b. In the present embodiment, the power circuit 15a is designed to supply the gate driver 15b with the on- and off-voltages that are to be applied to the gate electrode 8g of the TFT 8 through each scanning line 5. The gate driver 15b has a plurality of the aforementioned gate ICs 12a formed in parallel, and is designed to modulate the pulse width of the on-voltage applied to each scanning line 5, by means of a PWM (Pulse Width Modulation) signal.

In the present embodiment, the connection line 15c for binding the power circuit 15a of the scan drive section 15 and gate driver 15b is provided with a current detecting section 41 for detecting the current flowing therebetween. The current detecting section 41 can be designed to detect the current flowing through one or more scanning lines 5 out of lines L1 through Lx. The structure of the current detecting section 41 will be described later.

Each signal line 6 is connected to each reading circuit 17 formed inside the IC 16. Each of the IC's 16 is provided with a prescribed number of the reading circuits 17. Since a plurality of IC's 16 are provided, the reading circuits 17 in the number corresponding to that of the signal lines 6 can be provided.

The reading circuit 17 includes an amplification circuit 18, correlated double sampling circuit 19, analog multiplexer 21 and analog-to-digital converter 20. In FIGS. 7 and 8, the correlated double sampling circuit 19 is shown as CDS. In FIG. 8, the analog multiplexer 21 is not illustrated.

In the present embodiment, the amplification circuit 18 is composed of a charge amplification circuit, and includes an operation amplifier 18a, and a capacitor 18b and charge resetting switch 18c connected in parallel to the operation amplifier 18a. Further, the signal line 6 is connected to the reverse input terminal on the input side of the operation amplifier 18a of the amplification circuit 18. The reference voltage $V_o$ is applied to the non-reverse input terminal on the input side of the amplification circuit 18. The reference voltage $V_o$ is set at an appropriate value. In the present embodiment, the reference voltage $V_o$ is set at 0 volts.

Further, the charge resetting switch 18c of the amplification circuit 18 is connected to the main control section 22 and sub-control section 23. The on-off control is provided by the main control section 22. When the charge resetting switch 18c is off and the TFT 8 of the radiation detection element 7 is on (i.e., when the on-voltage is applied to the gate electrode 8g of the TFT 8 through the gate electrode 8g of the scanning line 5), the electric charge discharged from the radiation detection element 7 is fed and accumulated in such a way that the voltage value in conformity to the amount of electric charge accumulated is outputted from the output terminal of the operation amplifier 18a.

As described above, the amplification circuit 18 is designed to output the voltage in conformity to the amount of electric charge outputted from each radiation detection element 7, and to amplify the voltage by voltage conversion of the electric charge. When the charge resetting switch 18c has been turned on, a short circuit occurs to the input side and output side of the amplification circuit 18. The electric charge accumulated in the capacitor 18b is discharged and the amplification circuit 18 is reset.

The amplification circuit 18 can be configured to output the voltage in conformity to the electric charge outputted from the radiation detection element 7. Further, as shown in FIG. 8, power can be supplied to the amplification circuit 18 from the power supply section 42. In FIG. 7, the power supply section 42 is not illustrated.

A correlated double sampling circuit 19 (CDS) is connected to the output side of the amplification circuit 18. In the present embodiment, the correlated double sampling circuit 19 has a sample-holding function. The on-off state of the sample-holding function of the correlated double sampling circuit 19 is controlled by the pulse signal sent from the main control section 22.

To be more specific, after the amplification circuit 18 has been reset and the charge resetting switch 18c has been turned of the correlated double sampling circuit 19 receives the first signal from the main control section 22 when the image data is read from each radiation detection element 7, i.e., when the electric charge discharged from the radiation detection element 7 flows into the capacitor 18b and starts to be accumulated. At this time point, the voltage is maintained at the value of the voltage outputted from the amplification circuit 18.

After the lapse of a predetermined time from that time point, the electric charge discharged from the radiation detection element 7 flows into the capacitor 18b and is accumulated. At this time point, the second pulse signal from the main control section 22 is received. From this moment, the value of the voltage outputted from the amplification circuit 18 is again maintained, and the difference between these voltage values is outputted to the downstream side as image data.

The image data of each radiation detection element 7 outputted from the correlated double sampling circuit 19 is sent to the analog multiplexer 21, and is sequentially sent to the analog-to-digital converter 20 from the analog multiplexer 21. The image data is sequentially converted into the image data of digital value by the analog-to-digital converter 20 and is outputted to the storage section 43, wherein the image data is stored.

In the present embodiment, the main control section 22 includes a computer connected with an unillustrated CPU (Central Processing Unit), ROM (Read Only Memory), RAM (Random Access Memory) and input/output interface, as well as an FPGA (Field Programmable Gate Array) by means of buses.

In the present embodiment, the sub-control section 23 includes a microcomputer (also called a microprocessor). The sub-control section 23 to be used is characterized by power consumption smaller than that of the main control section 22.

In the following description of the present embodiment, the main control section 22 and sub-control section 23 are provided as control means for controlling each functional section of the radiographic imaging apparatus 1, as described above. The main control section 22 consuming a greater power is employed to control the processing that requires a great number of functional parts, as in the reading of image data from the radiation detection element 7 or in the transmission of image data. The sub-control section 23 that consumes less power than the main control section 22 is used to control other processing that can be executed by starting only a specific functional section, as in the resetting of the radiation detection element 7 or in the monitoring of the start of irradiation, thereby minimizing the unwanted waste of power.

It is also possible to make such arrangements that all the processing can be controlled by only one control section. The present invention is not restricted to the case wherein the main control section 22 and sub-control section 23 are separately installed.

In the present embodiment, the mode of operation of the main control section 22 and sub-control section 23 can be switched between the startup mode and suspension mode. In the present embodiment, the suspension mode is defined as the sleep mode wherein a small amount of power is supplied to accept only the start signal indicating the start of the operation from the sub-control section 23 in the case of the counterpart device, i.e., main control section 22, and from the main control section 22 in the case of the sub-control section 23. When the power of the radiographic imaging apparatus 1 has been turned off by the operator such as a radiological technician, the main control section 22 and sub-control section 23 are set to the OFF mode wherein no power is supplied at all.

In the present embodiment, when the power switch 36 has been depressed by the operator (FIG. 1) and the radiographic imaging apparatus 1 has been turned on, the sub-control section 23 is set to the startup mode, and the main control section 22 is set to the suspension mode, i.e., the sleep mode. Based on the current value detected by the current detecting section 41, the sub-control section 23 has detected the start and termination of irradiation to the radiographic imaging apparatus 1. Then the startup signal is sent to the main control section 22, which is started up. After the main control section 22 has been started, the sub-control section 23 is automatically suspended.

When the main control section 22 has terminated the operation of reading the image data from the radiation detection element 7 and transmitting the image data to an external device, a startup signal is sent from the main control section 22 to the sub-control section 23 so that the operation of the sub-control section 23 is started. At the same time, the main control section 22 automatically suspends its operation.

As described above, the main control section 22 is turned on only when reading the image data from the radiation detection element 7 and transmitting the image data to an external device, and is suspended otherwise to go into the sleep mode.

Figure 7:
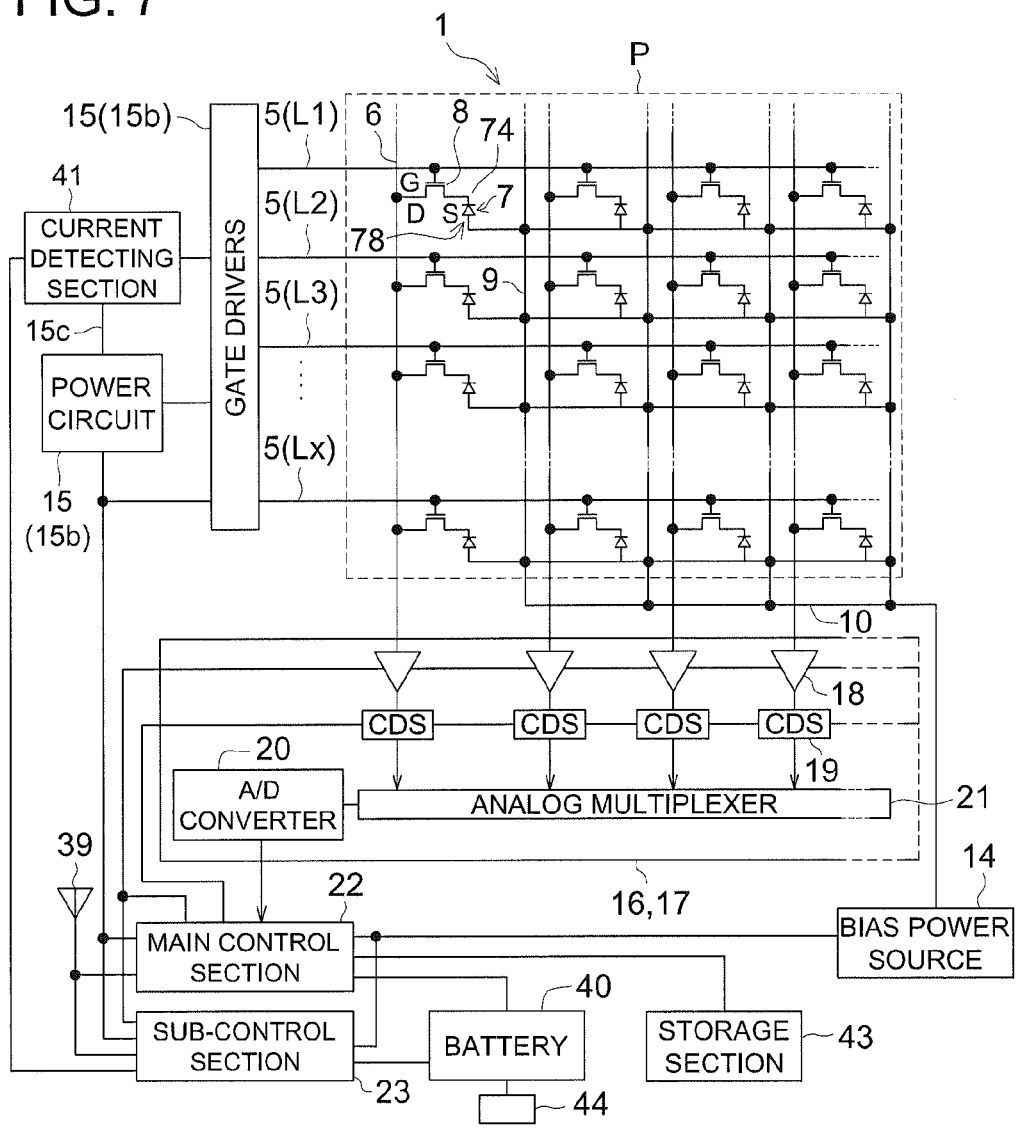
FIG. 7 is a block diagram showing the equivalent circuit of the radiographic imaging apparatus in the present embodiment.
Figure 8:
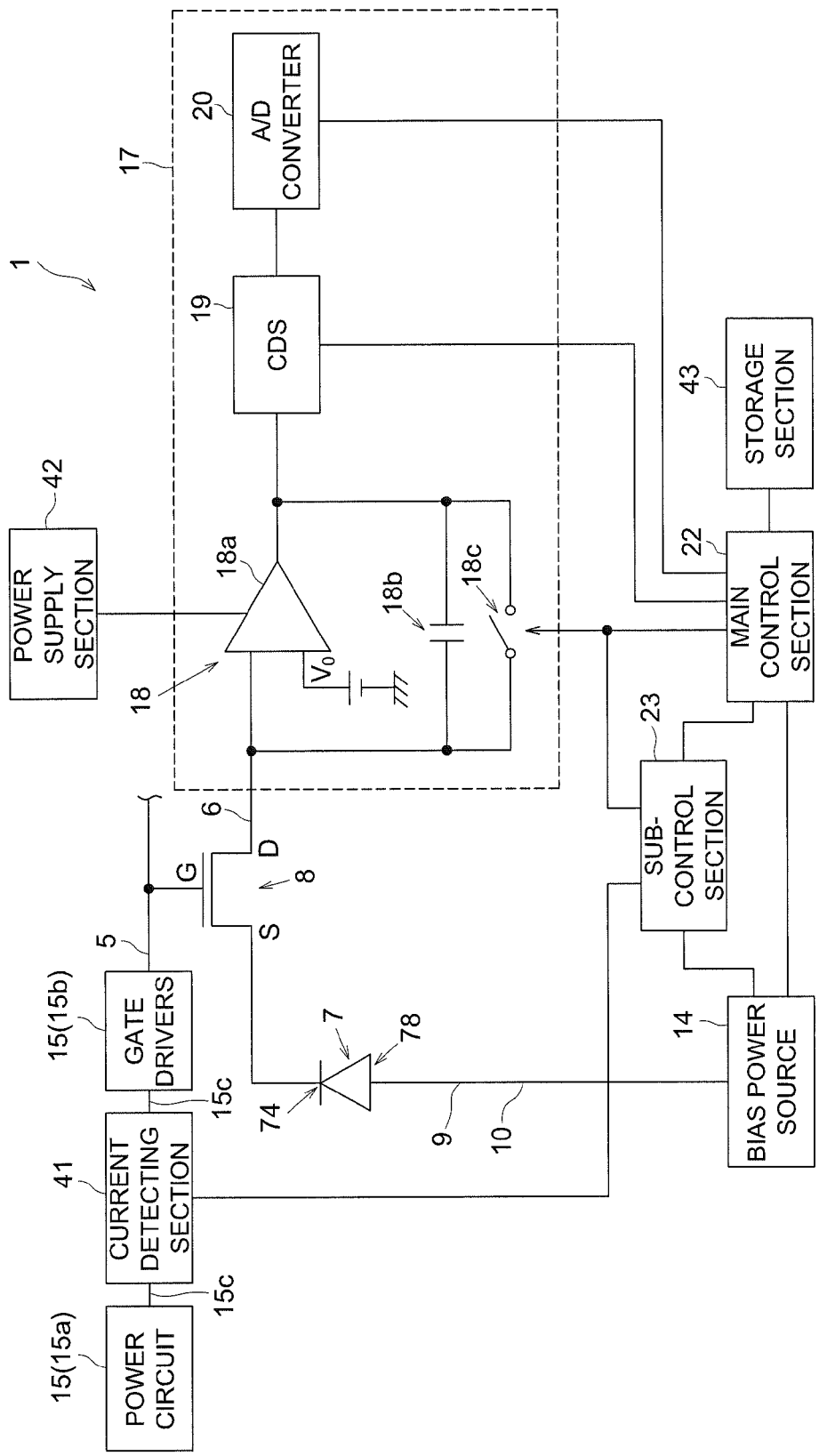
FIG. 8 is a block diagram showing the equivalent circuit for one pixel constituting the detector.

As shown in FIGS. 7 and 8, the sub-control section 23 is connected with the bias power source 14 and charge resetting switch 18c of the amplification circuit 18. Further, the sub-control section 23 is also connected with the power supply section 42, and the power circuit 15a and gate driver 15b of the scan drive section 15, although not illustrated in FIG. 8.

When the radiographic imaging apparatus 1 has been turned on and is set to the ON mode, the sub-control section 23 allows power to be supplied from the power supply section 42 to the amplification circuit 18 so that the amplification circuit 18 is started. Further, the sub-control section 23 turns on the charge resetting switch 18c. In this phase, no power is supplied to other functional sections of the reading circuit 17, i.e., the correlated double sampling circuit 19, analog-to-digital converter 20 or analog multiplexer 21.

The sub-control section 23 is connected with the scan drive section 15. The sub-control section 23 bias power source 14 applies bias voltage to each radiation detection element 7 through the bias line 9. At the same time, on-voltage is supplied from the scan drive section 15 to the scanning line 5, and on-voltage is applied to the gate electrode 8g of each TFT 8 connected to each scanning line 5. Thus, all the TFT 8 are turned on and the gates of all the TFT 8 are kept opened.

When the functional sections have been started, the excessive electric charge accumulated in the radiation detection element 7 passes through the TFT 8 and charge resetting switch 18c. From the output terminal side of the operation amplifier 18a of the amplification circuit 18, the excessive electric charge passes through the operation amplifier 18a to be discharged into the power supply section 42. In this manner, the radiation detection element 7 is reset.

In the present embodiment, the sub-control section 23 supplies power only to the functional sections wherein power is required to set the radiation detection element 7 and to detect current by the current detecting section 41 (to be described later), without supplying power to other places. This ensures that there is no unwanted waste of power.

Further, the sub-control section 23 is connected with the aforementioned current detecting section 41. Based on the current value detected by the current detecting section 41, the sub-control section 23 detects the start of irradiation.

The following describes the structure of the current detecting section 41. In the present embodiment, the current detecting section 41 is provided on the connection line 15c for connecting between the power circuit 15a and gate driver 15b of the scan drive section 15, as described above. The current detecting section 41 detects the current flowing between the power circuit 15a and gate driver 15b with the start of irradiation.

Figure 9:
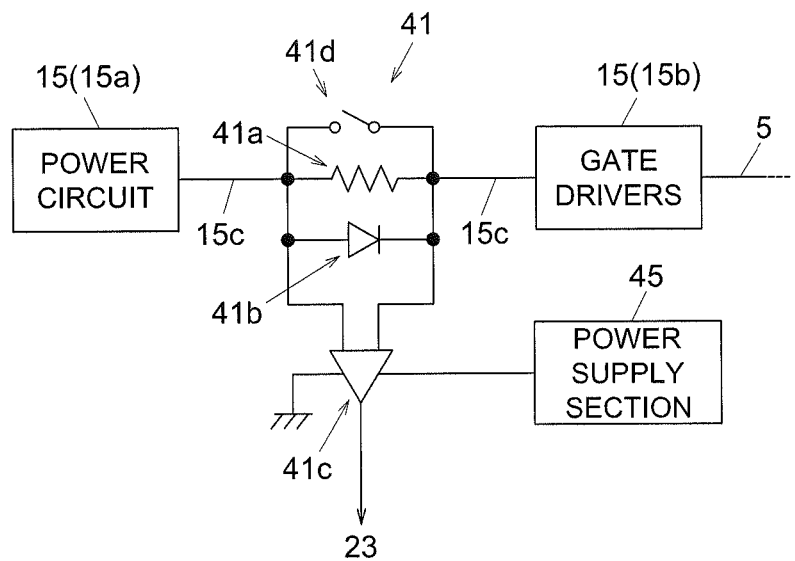
FIG. 9 is an equivalent circuit diagram showing the structure of the current detecting section.

To put it more specifically, in the present embodiment, the current detecting section 41 includes a resistor 41a having a prescribed resistance value serially connected to the connection line 15c connecting between the power circuit 15a and gate driver 15b of the scan drive section 15, a diode 41b connected in parallel thereto, and a differential amplifier 41c whose input terminals are connected to both ends of the resistor 41a, as shown in FIG. 9. Power is supplied to the differential amplifier 41c from the power supply section 45.

The current detecting section 41 uses a differential amplifier 41c to measure the voltage V across the resistor 41a. The current detecting section 41 measures the current flowing through the resistor 41a, i.e., the current flowing between the power circuit 15a and gate driver 15b, and converts this current into the voltage value V. This value is detected and outputted to the sub-control section 23.

A resistor 41a mounted on the current detecting section 41 and used in the present embodiment is a resistor having a resistance value capable of converting the current flowing through the connection line 15c into an appropriate voltage value V. The diode 41b is intended to detect an extensive dynamic range as in the radiation detection element. It is also possible to make such arrangements that only the diode 41b or resistor 41a is mounted.

Except when detecting the start and termination of irradiation, the current flowing between the power circuit 15a and gate driver 15b need not be detected by the current detecting section 41. Conversely, the resistor 41a of the current detecting section 41 disturbs supply of the on- or off-voltage to the gate driver 15b from the power circuit 15a. Accordingly, the current detecting section 41 is provided with a diode 41d for establishing a short circuit between both terminals of the resistor 41a wherever required, if the current detection is not required.

Figure 10:
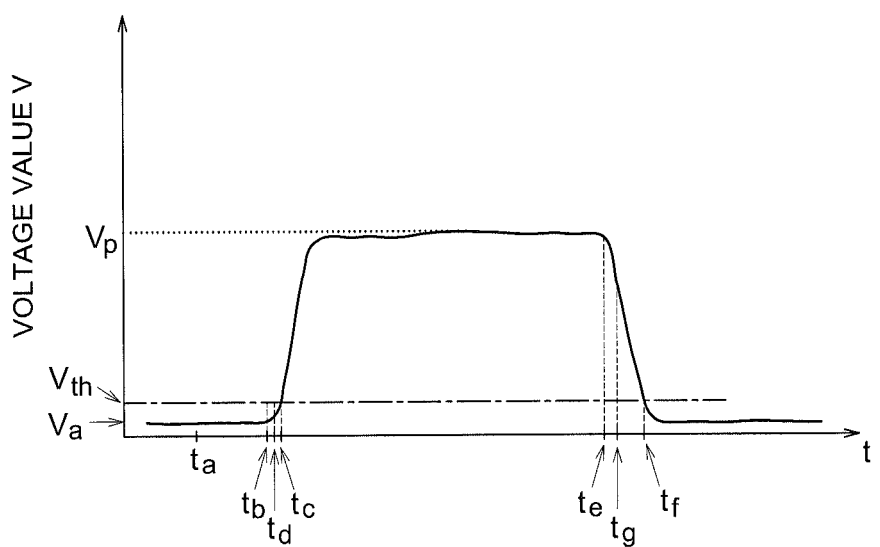
FIG. 10 is a chart representing an example of the voltage value equivalent to the current detected by the current detecting section.

When the radiographic imaging operation has started and radiation is applied to the radiation input surface R (FIG. 1) of the radiographic imaging apparatus 1 from an irradiation apparatus (not illustrated), there is an abrupt increase in the voltage value V equivalent to the current output from the differential amplifier 41c of the current detecting section 41 at time point tb when irradiation starts, as shown in FIG. 10. Thus, in the present embodiment, the sub-control section 23 is designed to detect the start of irradiation, for example, when the preset threshold value Vth has been exceeded (time tc in FIG. 10) due to an increase in the voltage value V outputted from the current detecting section 41, or when the increase rate of the voltage value V has exceeded the preset threshold value (time td).

Even when radiation is not applied to the radiographic imaging apparatus 1, a dark electric charge occurs inside the radiation detection element 7 due to the thermal excitation due to the head of the radiation detection element 7. Thus, before the radiation is applied to the radiographic imaging apparatus 1, a small voltage value Va (not zero volts) may be outputted from the current detecting section 41 at time to shown in FIG. 10.

In the present embodiment, when detecting the start and termination of irradiation to the radiographic imaging apparatus 1, off-voltage is applied to the gate electrode 8g of each TFT 8 from the scan drive section 15 through each scanning line 5 so that each TFT 8 is kept turned off. As will be described later, it is also possible to make such arrangements that, at least when detecting the start of irradiation, on-voltage is applied to the gate electrode 8g of each TFT 8 so that each TFT 8 is turned on.

Further, even when each TFT 8 is turned off, if irradiation has started, current flows between the power circuit 15a and gate driver 15b of the scan drive section 15 for the following reason.

As described above, when radiation is applied to the radiographic imaging apparatus 1, the radiation inputted into the radiographic imaging apparatus 1 is converted into an electromagnetic wave such as visible light by a scintillator 3. The converted electromagnetic wave reaches the i-layer 76 (FIG. 5) of the radiation detection element 7 located immediately below, with the result that an electron-hole pair is formed inside the i-layer 76 of the radiation detection element 7. In the radiation detection element 7, this causes a change in the potential of the first electrode 74 with respect to the second electrode 78.

In the present embodiment, bias voltage Vbias of a prescribed negative value is applied to the second electrode 78 from the bias power source 14 through the bias line 9 so that the potential is kept at a fixed level. Of the electron-hole pairs produced in the i-layer 76, the positive holes move toward the second electrode 78, while electrons move toward the first electrode 74. This results in the reduction in the potential on the first electrode 74. When the potential on the first electrode 74 of the radiation detection element 7 has been reduced, the potential on the side of the source electrode 8s ("S" in FIG. 8) of the TFT 8 in FIG. 8 is also reduced, accordingly.

In the TFT 8, a kind of capacitor is formed by the gate electrode 8g, source electrode 8s and insulating layer 71 (FIG. 5) between them. A parasitic capacitance is present between the gate electrode 8g and source electrode 8s. When a prescribed off-voltage is applied, and there is a reduction in the potential on the side of the source electrode 8s of the TFT 8 with respect to the gate electrode 8g of the TFT 8 without being subjected to any change in potential, there will be a change in the potential difference between the gate electrode 8g and source electrode 8s.

Thus, the electric charge corresponding to the potential difference having been changed is supplied to the gate electrode 8g of the TFT 8 through the scanning line 5. To be more specific, current flows through the scanning line 5. Thus, the current corresponding to the total volume of the current flowing through each scanning line 5 flows through the connection line 15c connecting between the power circuit 15a and gate driver 15b. Accordingly, even when each TFT 8 is kept turned off, the current running between the power circuit 15a and gate driver 15b (or voltage value V corresponding to thereto) with the start of irradiation can be detected by the current detecting section 41.

As described above, with the start of irradiation, current flows to each of the lines L1 through Lx in the scanning lines 5. The current detecting section 41 need not always be provided on the connection line 15c connecting between the power circuit 15a and gate driver 15b, as in the present embodiment. As described above, it is also possible to make such arrangements as to detect the current flowing through one or more scanning lines 5 out of the lines L1 through Lx. This arrangement detects the current running through the scanning line 5, and hence detects the start and termination of irradiation.

However, on the detecting section P, there will be an enormous number of the radiation detection elements 7 arranged in a two-dimensional array. Further, a great number of many scanning lines 5 are installed. This results in a relatively large current value on the connection line 15c connecting between the power circuit 15a and gate driver 15b. Thus, if current detecting section 41 is provided on the connection line 15c as in the present embodiment, the voltage value V corresponding to the current detected by the current detecting section 41 is provided with a sufficient S/N ratio to ensure accurate detection of the increase or decrease thereof.

The current caused to flow with the start of irradiation runs between the power circuit 15a and gate driver 15b, and through the scanning line 5. Not only that, the current in the equivalent amount flows between the source electrode 8s ("S" in FIG. 8) of the TFT 8 and radiation detection element 7, and between the radiation detection element 7 and bias power source 14.

In the meantime, upon completion of irradiation, generation of the electron-hole pair inside the radiation detection element 7 stops. This suspends the flowg of current through the scanning line 5 and the connection line 15c connecting between the power circuit 15a and gate driver 15b of the scan drive section 15. For example, upon completion of irradiation at time te, as shown in FIG. 10, the voltage value V corresponding to the current detected by the current detecting section 41 is suddenly reduced after time te.

Thus, in the present embodiment, the sub-control section 23 detects termination of irradiation when the voltage value V corresponding to the current outputted from the current detecting section 41 has been reduced below the threshold value Vth (time tf) after the start of irradiation has been detected, or when the decrease rate of the voltage value V has been reduced below the preset threshold value (time tg). The following description assumes that the irradiation startup time is tc in FIG. 10 and irradiation termination time is tf.

As described above, electron-hole pairs are generated in the i-layer 76 in proportion to the number of the photons in the radiation inputted into the i-layer 76 of the radiation detection element 7 or the electromagnetic wave inputted into the i-layer 76 of the radiation detection element 7 after the inputted radiation has been converted by the scintillator 3. This is accompanied by a change in the potential difference between the first electrode 74 and second electrode 78 of the radiation detection element 7 and the potential difference between the source electrode 8s and gate electrode 8g of the TFT 8. This causes a current flow through the connection line 15c connecting between the power circuit 15a and gate driver 15b of the scan drive section 15.

The dosage of radiation applied to the radiographic imaging apparatus 1 from the start of radiation to the termination thereof can be calculated by measuring the current value (or equivalent voltage value V) flowing through the connection line 15c.

It is also possible to make the following arrangements: For example, a step is taken to install an integrating circuit on the output terminal side of the differential amplifier 41c of the current detecting section 41 of FIG. 9 so as to calculate the voltage value V from the irradiation startup time "tc" to the irradiation termination time "tf" shown in FIG. 10 (or value obtained by subtracting a prescribed value equivalent to noise from the voltage value V), thereby calculating the dosage of radiation applied to the radiographic imaging apparatus 1. This arrangement ensures more accurate calculation of the dosage of radiation.

To remove the noise component more positively in the aforementioned arrangement, a further step can be taken to install a band-pass filter (frequency band-pass filter) that allows passage of only the data in the frequency band in a prescribed range without allowing the passage of the data of other frequencies by damping, for example, between the output terminal of the differential amplifier 41c of the current detecting section 41 and integrating circuit. Then band pass filtering processing is applied to the voltage value V equivalent to the current value outputted from the current detecting section 41. The results thereof are integrated to calculate the dosage of radiation.

To simplify the method of calculating the dosage of radiation, it is also possible to produce a sub-control section 23 having a peak holding function, for example, in such a way that the sub-control section 23 will calculate the dosage based on the time interval tf-tc from the start of irradiation to the termination of irradiation and the peak value of the current flowing through the connection line 15c detected by the current detecting section 41.

To put it more specifically, the sub-control section 23 detects the peak value Vp (FIG. 10) of the voltage value detected during the time from irradiation startup time "tc" to irradiation termination time "tf", and calculates the approximation M of the dosage of radiation applied to the radiographic imaging apparatus 1, based on the value obtained by multiplying the peak value Vp by the value obtained by subtracting a constant α from the time interval tf-tc from the start of irradiation to the termination of irradiation in conformity to the following formula (1).

$$M = a \times Vp \times (tf - tc - \alpha) \tag{1}$$

To get the approximation M of this radiation, a step is taken to approximate in a rectangular form the voltage value V from the rising portion after irradiation startup time "tc" in FIG. 10 to the falling portion before irradiation termination time "tf". Then the approximation M of this radiation is obtained as a value proportional to the area thereof. This method has an advantage in that calculation is made simply by detecting the irradiation startup time "tc" and irradiation termination time "tf", and then the detecting the peak value Vp. It should be noted that "a" indicates a preset constant in the aforementioned formula (1). The constant α is a preset constant for adjusting the error that may occur when a rectangular form is assumed in the transition of the voltage value V in a trapezoidal form.

The following describes the operation of the radiographic imaging apparatus 1 in the present embodiment.

In the radiographic imaging apparatus 1 of the present embodiment, the power switch 36 (FIG. 1) is depressed by the operator and the power of the radiographic imaging apparatus 1 is turned on. This starts up the sub-control section 23, while the main control section 22 is set in the suspension mode, i.e., sleep mode.

After having been turned on, the sub-control section 23 performs prescribed operations of resetting the radiation detection elements 7. To be more specific, the sub-control section 23 allows power to be supplied to only the amplification circuit 18 of the reading circuit 17 from the power supply section 42 (FIG. 8) so that the amplification circuit 18 is turned on. The sub-control section 23 starts the bias power source 14, and allows the on-voltage to be supplied to the scanning line 5 from the scan drive section 15 with the bias voltage applied to the radiation detection element 7 through the bias line 9 so that each TFT 8 connected to each scanning line 5 is turned on. Thus, excessive electric charge stored in the radiation detection element 7 is discharged to the power supply section 42 through the TFT 8 and amplification circuit 18. This procedure ensures the operation of resetting each radiation detection element 7 to be performed, while preventing power from being supplied to the correlated double sampling circuit 19 of the reading circuit 17 or analog-to-digital converter 20, and avoiding the unwanted waste of power.

Upon completion of the operation of resetting each radiation detection element 7, the sub-control section 23 allows the off-voltage to be applied to the gate electrode 8g of each TFT 8 from the scan drive section 15 through the scanning line 5, so that each TFT 8 is turned off. The power is supplied from the power supply section 45 (FIG. 9) to the differential amplifier 41c of the current detecting section 41 so that the switch 41d is turned off. Then the current detecting section 41 is started to monitor the voltage value V outputted from the differential amplifier 41c, namely, the voltage value V corresponding to the current flowing through the connection line 15c connecting between the power circuit 15a and gate driver 15b of the scan drive section 15.

When exposure of the radiographic imaging apparatus 1 to radiation has started, electron-hole pairs are provided on the i-layer 76 of the radiation detection element 7 in conformity to the dosage of the radiation having been applied, as described above. This causes a change in the potential of the first electrode 74 with respect to the second electrode 78 of the radiation detection element 7, with the result that current flows through the scanning line 5. As shown in FIG. 10, there is an abrupt increase in the voltage value V outputted from the current detecting section 41. The sub-control section 23 detects the increase in the voltage value V to identify the start of irradiation, as described above.

Upon completion of the irradiation, generation of electron-hole pairs is suspended in the radiation detection element 7. This results in an abrupt decrease in the voltage value V equivalent to the current detected by the current detecting section 41, as shown in FIG. 10. The sub-control section 23 detects the decrease in voltage value V to identify termination of irradiation.

As in the present embodiment, when a current detecting section 41 is provided to detect the current (voltage value V corresponding thereto) flowing through the connection line 15c, similarly to the case wherein a current detecting section is installed on the bias line 9 or connection line 10 in the conventional art, noise is generated by the current detecting section 41, and is applied to each scanning line 5 from the power circuit 15a of the scan drive section 15 through the gate driver 15b. The noise produced in the current detecting section 41 is superimposed on the off-voltage applied to the gate electrode 8g of each TFT 8.

As described above, when a current detecting section is installed on the bias line 9 as in the conventional art, the noise of voltage generated in the current detecting section is, so to speak, amplified by a greater parasitic capacitance C of the radiation detection element 7, and is turned into a greater noise charge. This is superimposed on the electric charge generated in the radiation detection element by irradiation.

However, the area wherein the source electrode 8s and gate electrode 8g of the TFT 8 are overlapped with each other is very small, as compared to the area of the light converging surface of the photo diode constituting the radiation detection element 7, as shown in FIG. 4. This increases the parasitic capacitance C on the photo diode portion of the radiation detection element 7, in contrast to a very small parasitic capacitance C formed of the source electrode 8s and gate electrode 8g of the TFT 8.

Thus, as in the present embodiment, when a current detecting section 41 is installed on the connection line 15c for connecting between the power circuit 15a and gate driver 15b of the scan drive section 15, the noise of the voltage generated in the current detecting section 41 is amplified only slightly by a very small parasitic capacitance C, with the result that the generated noise charge is very small.

Even if the very small noise charge produced in the area wherein the source electrode 8s and gate electrode 8g of the TFT 8 are overlapped with each other is transmitted to the radiation detection element 7, and is superimposed onto the electric charge occurring to the photo diode portion of the radiation detection element 7 due to irradiation, the impact thereof will be extremely small, as compared to that in the conventional art.

The present embodiment ensures that only a very small impact of voltage noise generated by the current detecting section 41 is superimposed on the finally obtained data read from the radiation detection element 7. This provides a positive reduction of the impact of noise charge, and eliminates the possibility of adversely affecting the quality of the finally obtained radiological image, the granularity thereof in particular.

Upon completion of detecting the start and termination of irradiation, the sub-control section 23 suspends supply of power to the differential amplifier 41c of the current detecting section 41 from the power supply section 45 so that the switch 41d is turned on, and both terminals of the resistor 41a are short-circuited, with the result that the function of the current detecting section 41 is suspended. Further, if the structure is configured to calculate the dosage of radiation applied to the radiographic imaging apparatus 1, the sub-control section 23 calculates the dosage in the procedure described above.

This is followed by the step of the sub-control section 23 sending the startup signal to the main control section 22 to read the image data from each radiation detection element 7 so that the main control section 22 is started and is turned on. When the main control section 22 has started, the sub-control section 23 need not be kept started. Accordingly, after having started the main control section 22, the sub-control section 23 automatically stops operation and goes into the sleep mode It is also possible to arrange such a configuration that a stop signal is sent to the sub-control section 23 from the main control section 22 having been started and turned on and, when the sub-control section 23 has received the stop signal from the main control section 22, the operation is suspended. If the operation of the sub-control section 23 is suspended when the main control section 22 has started as described above, unnecessary power is not sent to the sub-control section 23, and therefore, the unwanted waste of power is avoided.

When the main control section 22 has started, the main control section 22 starts the other required functional sections of the reading circuit 17 including the correlated double sampling circuit 19, analog-to-digital converter 20 and analog multiplexer 21. Then the electric charge is discharged from the radiation detection element 7, and the reading process of reading the image data is performed, as described above.

To be more specific, the main control section 22 sends the pulse signal to the scan drive section 15, and switches between the on- and off-states of the voltage applied to the gate electrode 8g of each TFT 8 from the scan drive section 15 through each scan drive section 15. At the same time, the main control section 22 controls the on/off operation of the charge resetting switch 18c of the amplification circuit 18 of the reading circuit 17, and controls the on/off states of the sample holding function thereof by sending the pulse signal to the correlated double sampling circuit 19. In this manner, the main control section 22 performs various such functions and reads the image data from the radiation detection element 7. The image data having been read out is stored in the storage section 43 (FIG. 7).

Further, upon completion of a series of radiographic imaging operations, the main control section 22 sends the image data stored in the storage section 43 to an external device through the antenna device 39. It is also possible to adopt such a structure that the image data is sent by the wired system such as a cable.

Upon completion of sending the image data to the external device, the main control section 22 starts the sub-control section 23, and is stopped or goes into the sleep mode automatically or by the stop signal from the sub-control section 23 having been started. In this case, the required information is sent to the sub-control section 23 from the main control section 22.

When the system goes into the mode where the radiographic imaging apparatus 1 is turned on in this manner, the sub-control section 23 having been started performs prescribed resetting operations, as described above. At the same time, the sub-control section 23 starts up the current detecting section 41 to continue to check if irradiation has started or not.

The aforementioned arrangement allows the main control section 22 to perform only the operation of image data reading or image data transmission wherein greater power consumption is required. Other operations such as monitoring of the irradiation are performed not by the main control section 22, but by the sub-control section 23 that consumes less power. This arrangement reduces the power consumption of the battery 40.

In some cases, a step is taken to perform the so-called dark reading operation wherein a dark charge is stored in each radiation detection element 7 after the image data has been read. The dark reading operation is performed in the same way as the aforementioned image data reading operation. Accordingly, for this operation, the main control section 22 is turned on at an appropriate timing. Other operations are also performed as appropriate. In this case, the main control section 22 is turned on to perform the operation, as required As described above, in the radiographic imaging apparatus 1 of the present embodiment, the current detecting section 41 for detecting the start of irradiation is installed between the power circuit 15a and gate driver 15b of the scan drive section 15 so as to detect the current flowing therebetween or through the scanning line 5.

In this arrangement, the parasitic capacitance C formed of the source electrode 8s and gate electrode 8g of the TFT 8 is much small than the parasitic capacitance C of the photo diode portion of the radiation detection element 7 that is inevitably increased by the greater area of the light converging surface. This fact can be utilized to drastically reduce the noise charge generated in the portion of the TFT 8 by the noise of the voltage generated in the current detecting section 41.

Thus, even if a very small noise charge produced in the TFT 8 is transferred to the radiation detection element 7 and is superimposed on the charge generated on the photo diode portion of the radiation detection element 7 by irradiation, the impact is extremely small, as compared to the case wherein the noise with respect to the bias voltage due to the current detecting section installed on the bias line 9 is amplified by the greater parasitic capacitance C of the radiation detection element 7, and a greater noise charge is superimposed, as in the conventional art.

The radiographic imaging apparatus 1 of the present embodiment ensures that only a very small impact of voltage noise generated by the current detecting section 41 is superimposed on the finally obtained data read from the radiation detection element 7. This provides a positive reduction of the impact of noise charge, and eliminates the possibility of adversely affecting the quality of the finally obtained radiological image, the granularity thereof in particular.

In the above description of the present embodiment, the operation of the current detecting section 41 continues after detecting the start of irradiation on the radiographic imaging apparatus 1. Based on the current value (voltage value V) detected by the current detecting section 41, detection is performed until irradiation terminates. However, when consideration is given to the impact of the noise produced by the current detecting section 41 as described above, the operation of the current detecting section 41 should be suspended after the start of irradiation has been detected. This reduces the noise impact more effectively.

Thus, when the sub-control section 23 detects the start of irradiation based on the current value outputted from the current detecting section 41 (or voltage value V corresponding thereto), it is possible to suspend the supply of power to the differential amplifier 41c of the current detecting section 41 from the power supply section 45 (FIG. 9) and to turn on the differential amplifier 41c, thereby stopping the function of the current detecting section 41.

In this case, the termination of irradiation cannot be detected based on the current value (or voltage value V) from the current detecting section 41. In this case, it is possible to adopt such a structure that a predetermined time is preset, and the sub-control section 23 identifies termination of irradiation after the lapse of a predetermined time subsequent to detection of the start of irradiation following an increase in the current value (or voltage value V) detected by the current detecting section 41.

This structure more effectively reduces the impact of the noise generated from the current detecting section 41 by suspending the operation of the current detecting section 41 after the start of irradiation has been detected. At the same time, if the irradiation is identified to have been terminated after the lapse of a predetermined time subsequent to detection of the start of irradiation, the subsequent operations such as resetting or dark reading can be performed properly.

In the above description of the present embodiment, at the time of detecting the start and termination of irradiation on the radiographic imaging apparatus 1, the off-voltage is applied to the gate electrode 8g of the each TFT 8 from the gate driver 15b through the scanning line 5, and the TFT 8 is turned off. When this configuration is adopted, however, a greater amount of the dark charge generated by the thermal excitation due to the heat of the radiation detection element 7 will be accumulated in the radiation detection element 7 in some cases, if a longer time is required before the irradiation is applied to the radiographic imaging apparatus 1 after the TFT 8 has been turned off.

To solve this problem, the following structure can be adopted in the present embodiment: Instead of the TFT 8 being turned off completely, the on- or off-voltage is regulated and applied to the gate electrode 8g of each TFT 8. When the start of irradiation is detected, each TFT 8 is slightly kept open. In this case, the voltage applied to the gate electrode 8g of the TFT 8 is regulated to the voltage level which is slightly (by a prescribed value) higher than the voltage value as a boundary wherein the off-state occurs when the voltage to be applied is reduced, namely, the voltage value as a boundary wherein the current flowing through the TFT 8 is reduced to just zero.

This structure ensures the start of irradiation to be accurately detected based on the current value (or voltage value V) detected by the current detecting section 41. Further, since each TFT 8 is slightly open, it is possible to remove a dark charge inside the radiation detection element 7 if there is any. This structure completely solves the problem of the dark charge being accumulated in the radiation detection element 7.

Further, instead of keeping each TFT 8 slightly open until the start of irradiation is detected, as described above, on-voltage can be applied to the gate electrode 8g of the TFT 8 until the start of irradiation is detected so as to open the TFT 8 positively. This structure provides a reliable means of removing the dark charge occurring inside each radiation detection element 7. This structure also ensures the start of irradiation to be identified based on the current value (or voltage value V) detected by the current detecting section 41.

However, when each TFT 8 is slightly opened, or is positively opened by application of on-voltage to the gate electrode 8g, if the TFT 8 is kept open subsequently, the charge produced inside each radiation detection element 7 by irradiation will flow out of the radiation detection element 7 through the TFT 8, with the result that the electric charge (image data) will not be accumulated in the radiation detection element 7.

To solve this problem, when the aforementioned structure is adopted, the sub-control section 23 applies the off-voltage to each scanning line 5 from the scan drive section 15 when having detected the start of irradiation from an increase in the voltage value V, and applies the off-voltage to the gate electrode 8g of the TFT 8 connected to each scanning line 5 so that all TFTs 8 are turned off.

When the aforementioned structure is adopted, it is also possible to arrange such a configuration that the current detecting section 41 is kept operating until the start of irradiation is detected, as in the present embodiment.

It is also possible to arrange such a configuration that the irradiation is assumed to have terminated after the lapse of a predetermined time subsequent to detection of the start of irradiation. When the voltage applied to the gate electrode 8g of each TFT 8 is switched over to the off-voltage, the operation of the current detecting section 41 is suspended. When a predetermined time has passed, termination of the irradiation is identified.

DESCRIPTION OF THE NUMERALS

1 Radiographic imaging apparatus
5 Scanning line
6 Signal line
7 Radiation detection element
8 ITT (switch section)
15 Scan drive section
15a Power circuit
15b Gate driver
23 Sub-control section (control section)
41 Current detecting section
41a Resistor
41d Switch
r Region
V Voltage value (voltage value corresponding to current)
Vp Peak value

The invention claimed is:

1. A radiographic imaging apparatus comprising:
a plurality of scanning lines;
a plurality of signal lines; arranged to cross each other;
a plurality of radiation detection elements two-dimensionally arranged in each region defined by the plurality of scanning lines and the plurality of signal lines;
a switch section which is arranged for each of the plurality of radiation detection elements and which is switched between on-state and off-state depending on a voltage applied to the connected scanning line, wherein an electric charge generated in the radiation detection element is maintained in the off-state and is released in the on-state;
a scan drive section having a gate driver that applies an on-voltage and an off-voltage to the switch section through the scanning line, and a power supply circuit that supplies said on-voltage and said off-voltage to the gate driver;
a current detecting section for detecting a current flowing between the power supply circuit and the gate driver or a current running through the scanning line; and
a control section for detecting at least a start of irradiation on a basis of a value of the current detected by the current detecting section.

2. The radiographic imaging apparatus of claim 1, wherein the current detecting section comprises: a resistor serially connected to a connection line connecting between the power supply circuit and the gate driver; and a switch which enables establishing a short circuit between both terminals of the resistor, and wherein the resistor and the switch are configured so that when detecting the start of irradiation, the short circuit established by the switch is released, and in other case, the short circuit between the both terminals of the resistor is established by the switch.

3. The radiographic imaging apparatus of claim 2, wherein the control section detects the start of irradiation when a current value detected by the current detecting section increases.

4. The radiographic imaging apparatus of claim 3, wherein the control section identifies termination of the irradiation after a lapse of a predetermined time subsequent to detection of the start of irradiation following an increase in the current value detected by the current detecting section.

5. The radiographic imaging apparatus of claim 1, wherein the control section detects the termination of irradiation when a current value detected by the current detecting section decreases.

6. The radiographic imaging apparatus of claim 5, wherein the control section calculates a dosage of radiation irradiated based on a time interval from the start of irradiation to the termination of irradiation and a peak value of the current detected by the current detecting section.

7. The radiographic imaging apparatus of claim 5, wherein the control section calculates a dosage of radiation irradiated as an integrated value of the current detected by the current detecting section during a time interval from the start of irradiation to the termination of irradiation.

8. The radiographic imaging apparatus of claim 5, wherein the control section calculates a dosage of radiation irradiated as an integrated value of values subject to a band pass filtering processing is applied to the current detected by the current detecting section during a time interval from the start of irradiation to the termination of irradiation, and.

9. The radiographic imaging apparatus of claim 1, wherein the switch section is maintained in the off-state when detecting the start of irradiation.

10. The radiographic imaging apparatus of claim 4, wherein when detecting the start of irradiation, a voltage higher than a boundary voltage value by a predetermined value is applied to the switching section, wherein the boundary voltage value is a value of the applied voltage with which the off-state occurs when the applied voltage is reduced.

* * * * *